(12) United States Patent
Hagiwara

(10) Patent No.: US 6,328,704 B1
(45) Date of Patent: Dec. 11, 2001

(54) SUCTION CUP FOR WEIGHT REDUCTION

(76) Inventor: Hidenori Hagiwara, 9-17, Ohoka 3-chome, Minami-ku, Yokohama-shi, Kanagawa-ken (JP)

(*) Notice: Subject to any disclaimer, the term of this patent is extended or adjusted under 35 U.S.C. 154(b) by 0 days.

(21) Appl. No.: 09/462,054

(22) PCT Filed: Jun. 30, 1998

(86) PCT No.: PCT/JP98/02914

§ 371 Date: Dec. 29, 1999

§ 102(e) Date: Dec. 29, 1999

(87) PCT Pub. No.: WO99/02116

PCT Pub. Date: Jan. 21, 1999

(30) Foreign Application Priority Data

Jul. 11, 1997 (JP) ................................................... 9-186324

(51) Int. Cl.[7] .................................................. A61H 7/00
(52) U.S. Cl. .................................... 601/6; 601/7; 601/10; 601/133
(58) Field of Search .................................. 601/6, 7, 9, 10, 601/11, 12, 13, 14, 133

(56) References Cited

U.S. PATENT DOCUMENTS

| | | | |
|---|---|---|---|
| 4,748,973 | * | 6/1988 | Cho ........................................ 601/10 |
| 5,897,512 | * | 4/1999 | Zagame .................................... 601/6 |

* cited by examiner

*Primary Examiner*—Michael A. Brown
*Assistant Examiner*—Benjamin K. Koo
(74) *Attorney, Agent, or Firm*—Bierman, Muserlian and Lucas

(57) ABSTRACT

Unwanted subcutaneous fat of a part of the body to be slimmed down is dissipated using a suction cup (1).

A plurality of suction holes (5, 6) having different sucking directions are arranged close together in an opening section of the suction cup (1) to be tightly fitted to part of the body to be slimmed down, so as to twist subcutaneous fat of a part of the body to be slimmed down.

5 Claims, 8 Drawing Sheets

SUCTION CUP FOR WEIGHT REDUCTION

TECHNICAL FIELD TO WHICH THE INVENTION BELONGS

The present invention relates to a suction cup for weight reduction, for reducing subcutaneous fat at parts of the body to be slimmed down.

BACKGROUND OF THE INVENTION

Suction therapy that draws blood congestion in internal portions of an affected area into an outer layer, by decompressing the inside of a suction cup, known as a sucker or suction ball using a suction pump or the like, with an opening section of the suction cup tightly adhered to an affected part, or alternatively by decompressing the inside of the suction cup by causing combustion of alcohol etc. inside the cup, and thus sucking in the affected area, and removing congestion of the affected part using an excretion action of remaining blood, is well known.

A cosmetic weight loss method has also been proposed that employs suction therapy that causes dissipation of unnecessary subcutaneous fat by sucking part of the body having excessive subcutaneous fat to be slimmed down into a suction cup.

With this cosmetic weight loss method, there is normally some desire for substantial weight reduction, and even if this type of suction therapy is applied to a cosmetic weight reduction method there is a desire for even more substantial weight reduction.

In view of the above described situation, the object of the present invention is to provide a suction cup for weight loss that can be expected to bring about even more substantial weight reduction.

DISCLOSURE OF THE INVENTION

According to the present invention, a suction cup for weight reduction is provided with an open-ended section that is tightly fitted against a part of the body to be slimmed down, and constructed so that the part of the body to be slimmed down is sucked in by decompressing the inside of the suction cup, having means for sucking in and twisting the part of the body to be slimmed down provided in the open-ended section.

The means for sucking in and twisting the part of the body to be slimmed down be formed of a plurality of suction holes having mutually different sucking directions provided close together.

The plurality of suction holes can be formed in a suction body provided integrally with the suction cup, but are preferably formed in a suction body which is detachable from the body of the suction cup.

The means for sucking in and twisting the part of the body to be slimmed down can also include pressing means for partially pressing the part of the body to be slimmed down.

The inside of the suction cup can be decompressed by burning alcohol etc. inside the cup, but the suction cup is preferably provided with a decompressing section connected to a suction pump via a hose. In that case, a non-return valve for preventing air flowing into the inside of the cup is housed in the decompressing section, and the hose is preferably detachable.

According to the present invention, because subcutaneous fat tissue is twisted and compressed by providing means for sucking in and twisting subcutaneous fat of a part of the body to be slimmed down in an open-ended section tightly fitted against the body, unwanted subcutaneous fat at the part of the body to be slimmed down is caused to dissipate and can be effectively removed.

The means for sucking in and twisting subcutaneous fat of a part of the body to be slimmed down can be formed of a plurality of suction holes having mutually different sucking directions provided close together, which means that subcutaneous fat at the part of the body to be slimmed down is twisted between adjacent holes, and so excellent weight reduction can be expected.

In this case, if the plurality of sucking holes are formed in a suction body separate from the cup body and this suction body is detachable from the cup body, it becomes possible to vary the number of suction holes and/or suction bodies having different sucking performance as required.

Also, by providing pressing means for partially pressing the part of the body to be slimmed down, subcutaneous fat is twisted between sucked in sections and pressed sections, which means that weight reduction effects can be expected.

Further, with respect to the structure for decompressing the inside of the suction cup using a suction pump, when a non-return valve for preventing air flowing into the inside of the cup is housed in the decompressing section, it is possible to maintain a decompressed state inside of the cup even if a hose connected to the decompressing section is taken off, by closing the non-return valve, which means that a number of suction cups can be placed one at a time on a number of parts of the body to be slimmed down, and these suction cups can put into a decompressed state while sequentially detaching hoses connected to a single suction pump.

PREFERRED EMBODIMENT OF THE INVENTION

Embodiments of the present invention will now be described in detail in the following with reference to the drawings.

Figure 1:
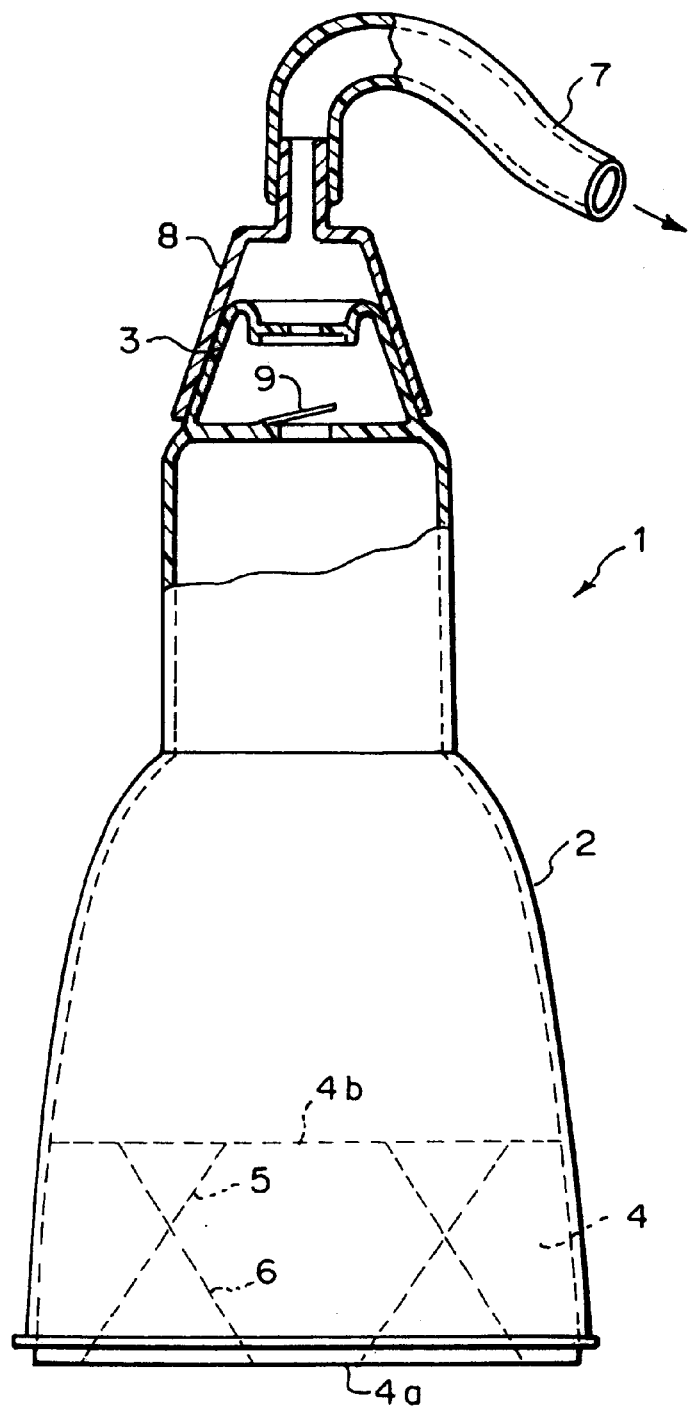
FIG. 1 is a front elevation of an embodiment of a suction cup for weight reduction of the present invention showing part of the suction cup in cross section.

As shown in FIG. 1, a suction cup for weight reduction 1 comprises a bell shaped cup body 2 opening downwards, a substantially radial decompressing section 3 formed integrally with an upper section of the cup body 2, and a suction body 4 formed as a separate body from the cup body 2 and fitted into the inside of the cup body 2 from an opening section of the cup body 2.

The suction body 4 is provided with two closely positioned suction holes 5 and 6 penetrating from a lower surface 4a fitting tightly against the skin surface of apart of the body to be slimmed down to an upper surface 4b of the inside of the cup body 2, and the lower surface 4a of the suction body 4 forms an opening section of the suction cup 1.

On the other hand, one end of a hose 7 is connected to a suction pump (not shown in the drawings) while the other end is detachably fitted into the decompressing section 3 formed integrally with an upper part of the cup body 2, and a non-return valve 9 for preventing air from flowing into the inside of the cup body 2 is housed in the decompressing section 3. After the cup body 2 has been decompressed using the suction pump, the decompressed state inside the cup body 2 can be maintained even if a connecting case 8 is taken off the decompressing section 3.

Accordingly, a suction cup can be placed at each of a number of parts of the body to be slimmed down, and these suction cups can be put into a decompressed state while sequentially detaching hoses connected to a single suction pump.

Figure 2:
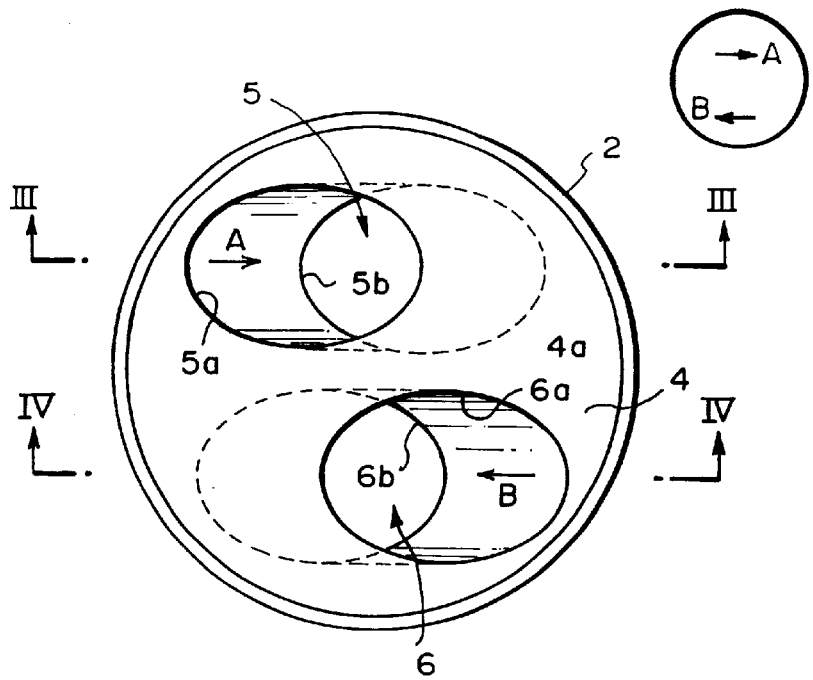
FIG. 2 is a bottom view of the suction cup of the first embodiment.
Figure 3:
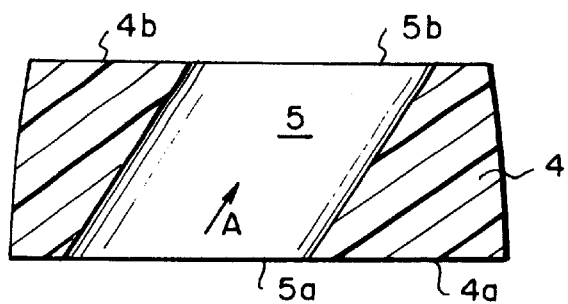
FIG. 3 is a cross sectional drawing of a suction body taken along line III—III of FIG. 2.
Figure 4:
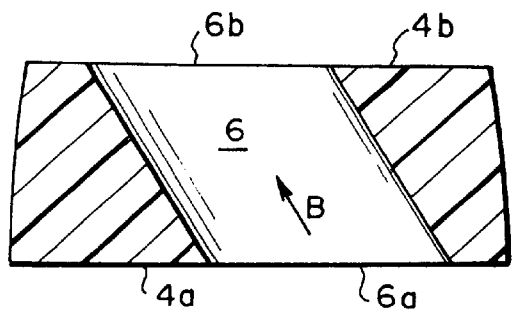
FIG. 4 is a cross sectional drawing of a suction body taken along line IV—IV of FIG. 2.

As can be clearly seen in FIG. 2, suction holes 5 and 6 formed in the suction body 4 have an elliptical cross section, and openings 5a and 5b in the lower surface 4a of the suction cup 4 are provided close together. Also, as can be clearly seen in FIG. 3 and FIG. 4, the suction holes 5 and 6 extend diagonally in different directions towards openings 5b and 6b in the upper surface 4b of the suction cup 4.

Accordingly, if the lower surface 4a of the suction cup 4 is made to fit tightly against the skin surface at a part of the body to be slimmed down, the connecting case 8 is fitted to the decompression terminal end 3 and the inside of the suction cup 2 decompressed using a suction pump, a part of the body to be slimmed down facing the opening 5a of the suction hole 5 is sucked in the direction of arrow A, and part of the body to be slimmed down facing the opening 6a of the suction hole 6 is sucked in the direction of arrow B. Subcutaneous fat at the region between the openings 5a and 5b is therefore compressed so as to twist, with the result that unwanted subcutaneous fat at the part of the body to be slimmed down can be effectively dissipated.

In FIG. 2, a small circle with arrows representing directions of suction is attached beside a bottom view of the suction cup, and this is the same for the following embodiments. However, the suction directions are indicated only by arrows in FIG. 1 and FIG. 12.

In the embodiment described above, the decompressing section 3 is connected via a hose 7 to the suction pump in order to decompress the inside of the cup body 2, but it is also possible to use a manual pump instead of the suction pump.

Also, instead of providing the decompression terminal end in the cup body 2, it is possible to decompress the inside of the cup body 2 by burning alcohol etc. inside the cup body 2, as is used in the suction therapy of the related art. In this case, if the inner wall surface of the cup body 2 is soaked in alcohol, and the cup body 2 is quickly laid upside down in the part of the body to be slimmed down after the alcohol is ignited, oxygen inside the cup body 2 is consumed and the flame is extinguished, the cup body is decompressed and the part of the body to be slimmed down is sucked in.

Figure 5:
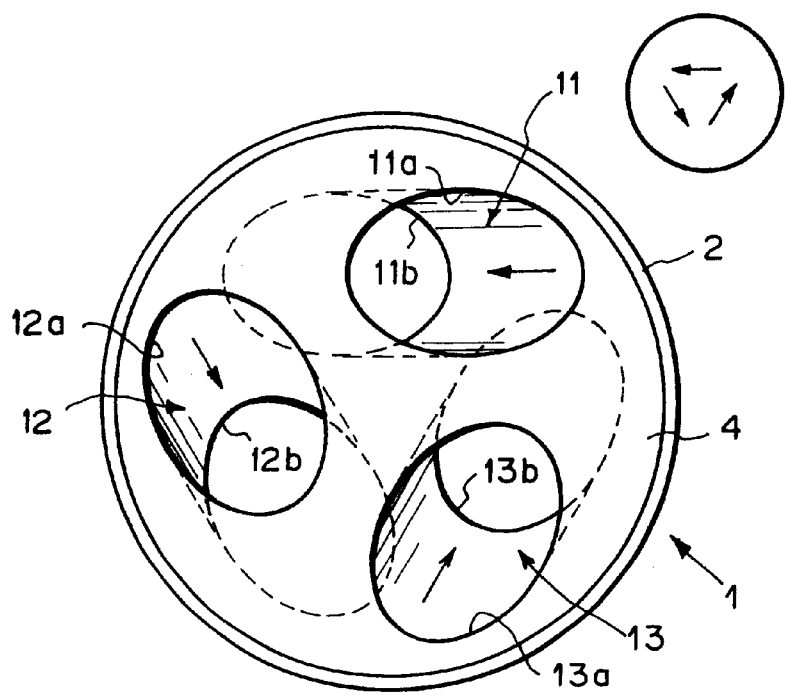
FIG. 5 to FIG. 12 are bottom views of other embodiments of suction cups for weight reduction of the present invention.
Figure 6:
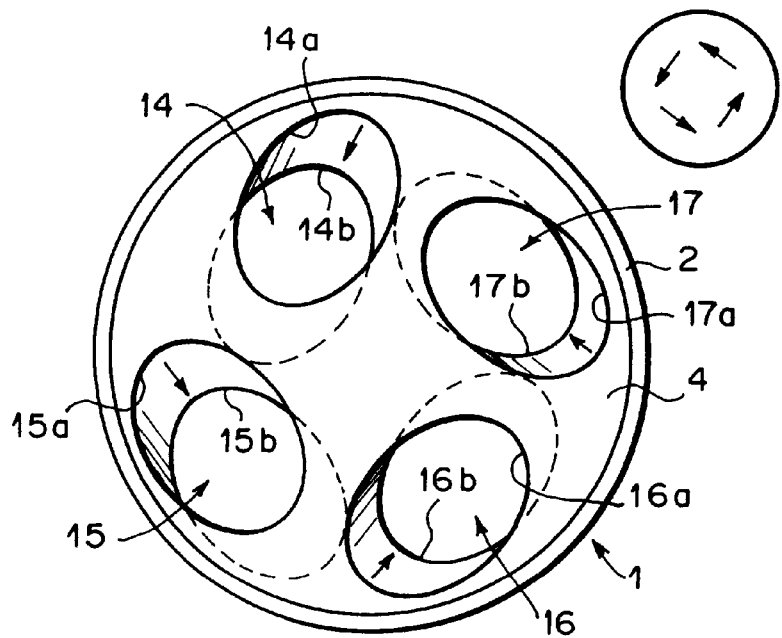

In the above described embodiment, a suction body 4 provided with two suction holes 5 and 6 is used, but the number of suction holes is not limited to two, and it is possible to use a suction body 4 with three or more suction holes, as shown in the bottom view of FIG. 5 and FIG. 6, corresponding to FIG. 2.

Specifically, in FIG. 5 three suction holes 11–13 are formed in the suction body 4. Here, reference numerals 11a–13a represent opening sections of suction holes opening into the lower surface 4b of the suction body 4. In this case also, the suction holes 11–13 have different suction directions, as shown by the arrows, so as to twist the subcutaneous fat of the part of the body sucked in.

Also, in FIG. 6 four suction holes 14–17 are formed in the suction body 4. Here, reference numerals 14a–17a represent opening sections of suction holes opening into the lower surface 4a of the suction body 4, while reference numerals 14b–17b represent opening sections of suction holes opening into the upper surface 4b of the suction body 4. In this case also, the suction holes 14–17 have suction directions set, as shown by the arrows, so as to twist the subcutaneous fat of the part of the body sucked in.

These suction holes 4 are preferably formed integrally with, and not separate from, the cup body 2, but it is possible to form the suction holes 4 separate from the cup body 2 or detachable from the cup body 2, which means that it is possible to change the number of suction holes or to change to a suction body 4 having different sucking characteristics, as required.

Figure 7:
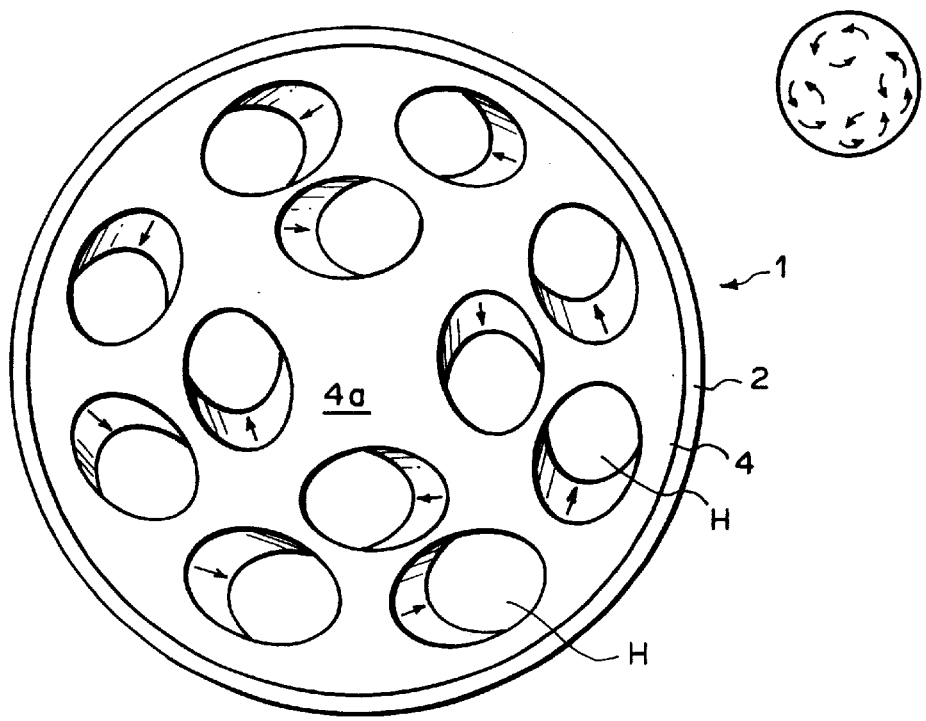
Figure 8:
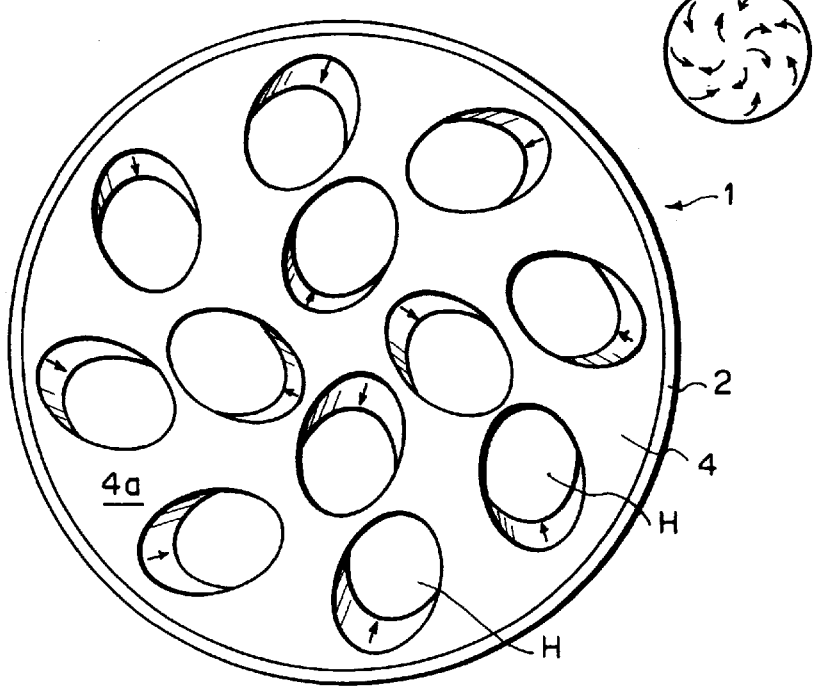

FIG. 7 and FIG. 8 are bottom views showing the case where the suction body 4 of the suction cup 1 has different suction directions and is provided with a plurality (ten in FIG. 7, twelve in FIG. 8) of suction holes H. In this case, the lower section of the cup body 2 and the cup body 4 are formed having a larger surface area than the embodiments shown in FIG. 2, FIG. 5 and FIG. 6.

Figure 9:
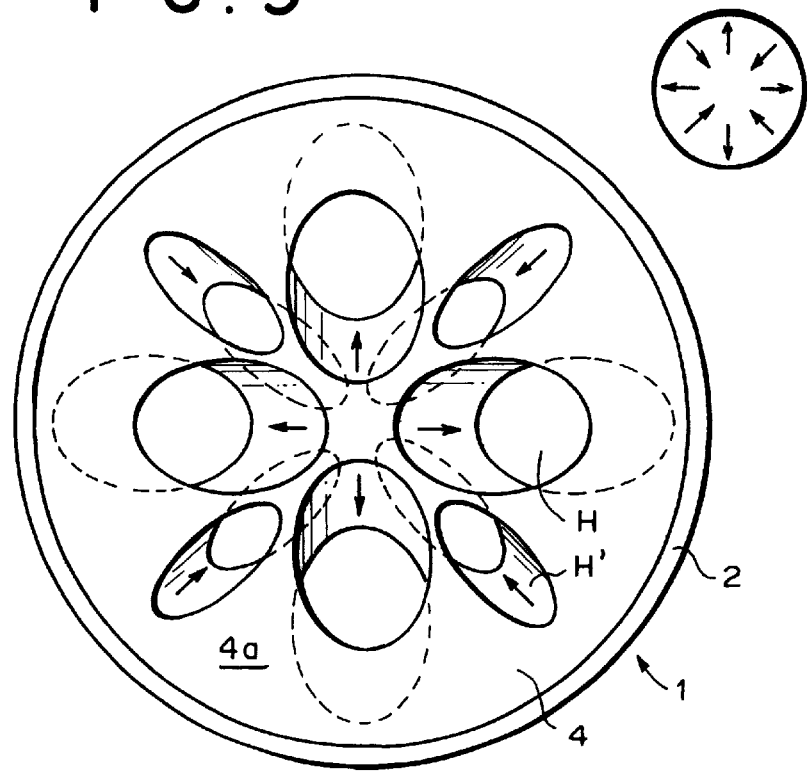

FIG. 9 shows the case of a combination of four suction holes H and four suction holes H' formed larger than and in different shapes to the four suction holes H.

Figure 10:
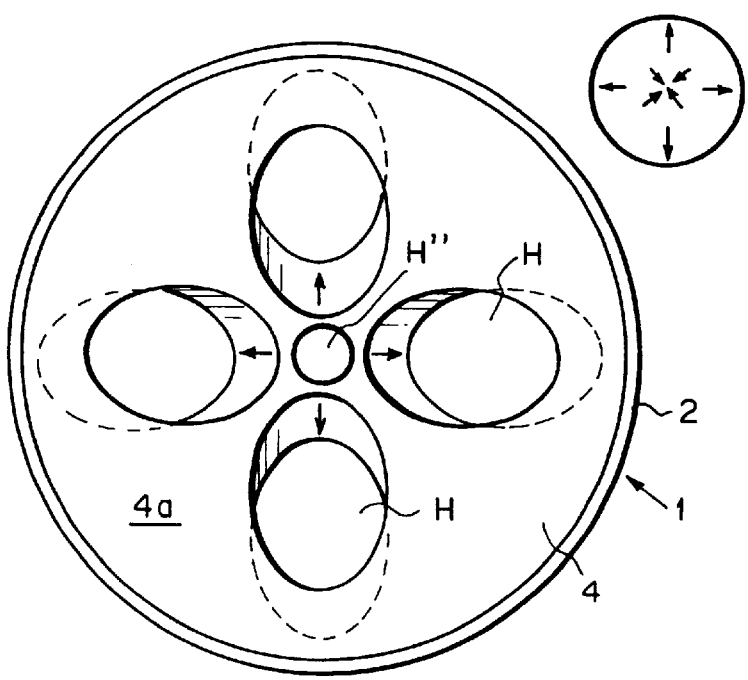

FIG. 10 shows an embodiment having a small suction hole H" having an upward sucking direction arranged in the middle of four suction holes H having sucking directions spreading outwards.

Figure 11:
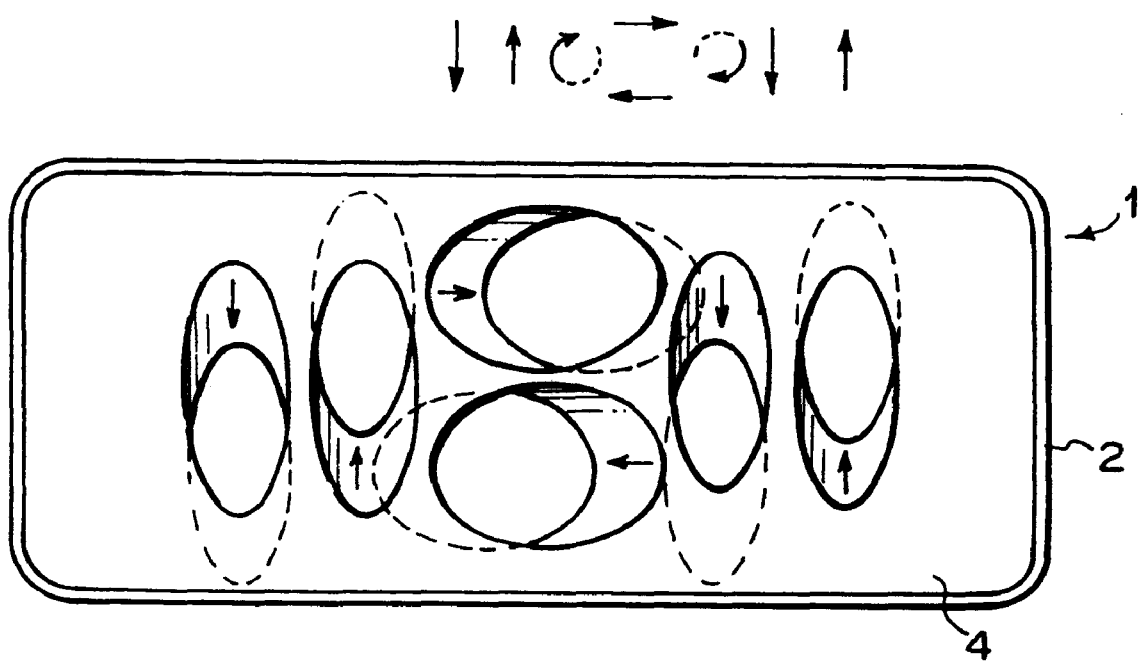
Figure 12:
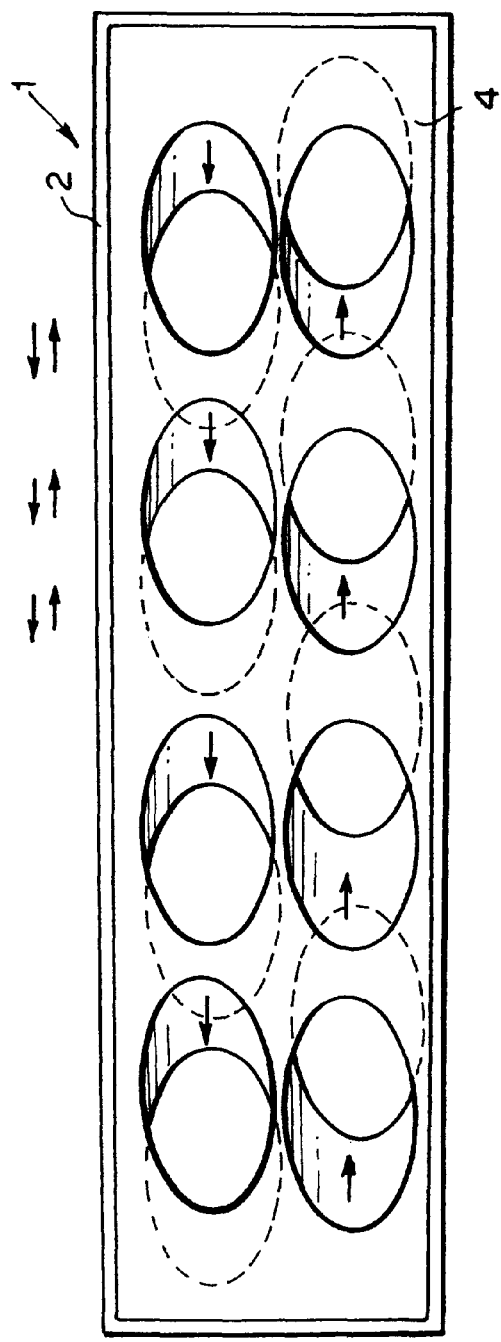

In the above described embodiments, the lower part of the cup body 2 and the bottom surface of the suction body 4 are circular in shape, but are not limited to being circular, and can also be rectangular, as shown in FIG. 11 and FIG. 12.

Figure 13:
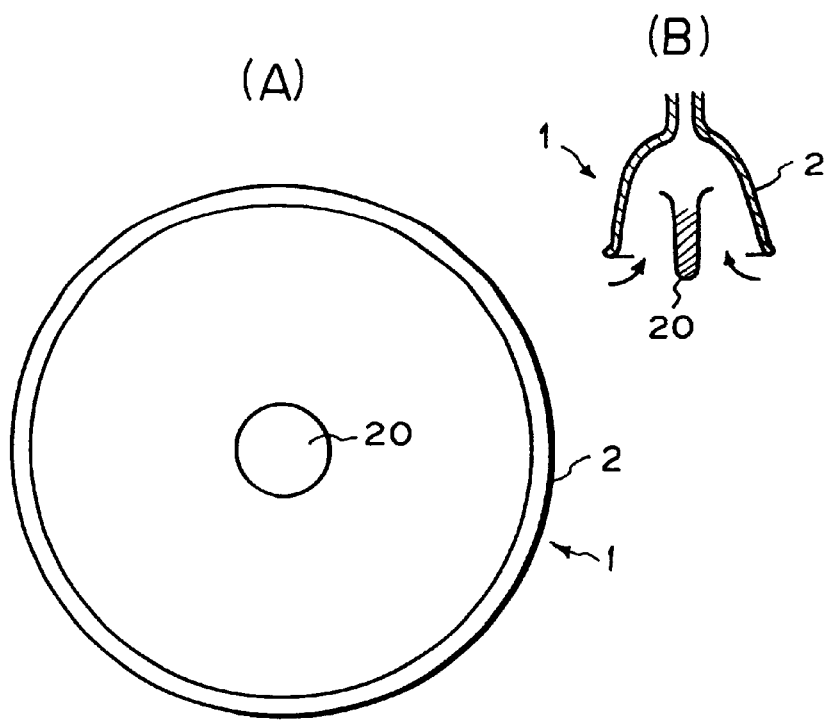
FIG. 13 and FIG. 14 are bottom views and schematic cross sectional views of yet still further embodiments of suction cups for weight reduction of the present invention.
Figure 14:
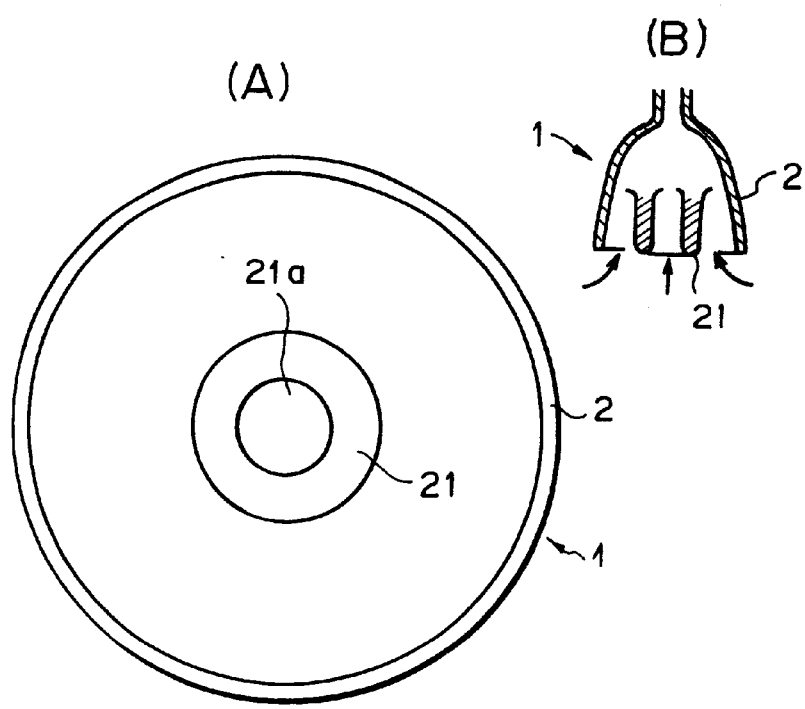

The embodiments shown in FIG. 1 to FIG. 12 have means for sucking, so as to twist subcutaneous fat of a part of the body to be slimmed down, formed of a plurality of suction holes opening out close to the lower surface 4a of the suction body 4, and having different sucking directions, but it is also possible to provide pressing means in the cup body 2 for partially pressing the part of the body, instead of using the suction body 4, as means for twisting the subcutaneous fat of the part of the body to be slimmed down, as shown in FIG. 13 and FIG. 14. In FIG. 13 and FIG. 14, drawing (A) is a bottom view and drawing (B) a schematic cross sectional view.

In FIG. 13, the pressing means for partially pressing the part of the body to be slimmed down comprises a single rod-like projection 20 hanging down from the middle of the cup body 2 and protruding slightly downwards from an opening of the cup body 2. Pressure stimulation is imparted to the part of the body to be slimmed down by this rod-like projection 20, and by sucking an area surrounding the rod-like projection 20 subcutaneous fat is twisted between the part pressed by the projection 20 and a part that is sucked in, which means that excellent weight loss effects are obtained.

In FIG. 14, a hollow cylinder 21 is used as the pressing means instead of the rod-like projection 20, and the weight reduction effect is improved by also sucking from a central hole 21a in the cylinder 21.

It is also possible to provide projections in the region between openings of suction holes of the lower surface 14a of the suction body 4 provided with a plurality of suction holes, as pressing means.

What is claimed is:

1. A suction cup for weight reduction provided with an opening section for fitting tightly to a part of the body to be slimmed down, and formed so as to suck in the part of the body to be slimmed down by internal decompression, wherein suction means is provided in the opening section adjacent the part of the body to be slimmed down, said suction means including a plurality of suction channels which are arranged close to each other and extend diagonally through said suction means in different directions so as to twist subcutaneous fat of the part of the body to be slimmed down.

2. The suction cup for weight reduction as defined in claim 1, wherein the plurality of suction channels are formed in a suction body detachable from a cup body.

3. The suction cup for weight reduction as defined in claim 2 wherein a decompressing section connected via a hose to a suction pump is provided as internal decompression means.

4. The suction cup for weight reduction as defined in claim 1, wherein a decompressing section connected via a hose to a suction pump is provided as internal decompression means.

5. The suction cup for weight reduction as defined in claim 4, wherein a non-return valve for preventing air flowing to the cup section is housed in the decompressing section, and the hose is detachable.

* * * * *

UNITED STATES PATENT AND TRADEMARK OFFICE
CERTIFICATE OF CORRECTION

PATENT NO.   : 6,328,704 B1                                                               Page 1 of 1
DATED        : December 11, 2001
INVENTOR(S)  : Hidenori Hagiwara It is certified that error appears in the above-identified patent and that said Letters Patent is hereby corrected as shown below:

Column 6,
Line 14, add claim 6:
-- 6.    The suction cup for weight reduction as defined in claim 3 wherein a non-return valve for preventing air flowing to the cup section is housed in the decompressing section, and the hose is detachable. --

Signed and Sealed this

Twenty-fourth Day of December, 2002

JAMES E. ROGAN
*Director of the United States Patent and Trademark Office*